US007351837B1

(12) United States Patent
McElhanon et al.

(10) Patent No.: US 7,351,837 B1
(45) Date of Patent: Apr. 1, 2008

(54) THERMALLY CLEAVABLE SURFACTANTS WITHOUT DEPROTONATION

(75) Inventors: James R. McElhanon, Manteca, CA (US); Gregory M. Jamison, Albuquerque, NM (US); Timothy M. Long, Evanston, IL (US); Douglas A. Loy, Tucson, AZ (US); Kamyar Rahimian, Albuquerque, NM (US); Blake A. Simmons, San Francisco, CA (US); Chad L. Staiger, Albuquerque, NM (US); David R. Wheeler, Albuquerque, NM (US); Thomas Zifer, Manteca, CA (US)

(73) Assignee: Sandia Corporation, Livermore, CA (US)

( * ) Notice: Subject to any disclaimer, the term of this patent is extended or adjusted under 35 U.S.C. 154(b) by 184 days.

(21) Appl. No.: 11/387,542

(22) Filed: Mar. 22, 2006

Related U.S. Application Data (63) Continuation-in-part of application No. 10/866,475, filed on Jun. 10, 2004, now Pat. No. 7,022,861.

(51) Int. Cl.
*C07D 491/18* (2006.01)
(52) U.S. Cl. .................................................. 548/431
(58) Field of Classification Search ................ 548/431
See application file for complete search history.

(56) References Cited

U.S. PATENT DOCUMENTS

| 6,271,335 | B1 | 8/2001 | Small et al. ................ 528/170 |
| 6,337,384 | B1 | 1/2002 | Loy et al. .................... 528/393 |
| 6,403,753 | B1 | 6/2002 | Loy et al. ..................... 528/73 |
| 6,600,076 | B1 | 7/2003 | Abbott et al. ................ 568/21 |
| 2003/0116272 | A1 | 6/2003 | Aubert | |

FOREIGN PATENT DOCUMENTS

| EP | 0 758314 | 9/1999 |
| WO | WO 97/14402 | 4/1997 |
| WO | WO 99/05241 | 2/1999 |
| WO | WO 02/064945 | 8/2002 |
| WO | WO 02/097393 | 12/2002 |

OTHER PUBLICATIONS

McElhanon, JR; Zifer, T; Kline, SR; Wheeler, DR; Loy, DA; Jamison, GM; Long, TM; Rahimian, K.; and Simmons, BA; "Thermally Cleavable Surfactants Based on Furan-Maleimide Diels-Alder Adducts," *Langmuir*, 2005, vol. 21, pp. 3259-3266.
Aubert J.; "Thermally Removable Epoxy Adhesives Incorporating Thermally Reversible Diels-Alder Adducts" *Journal of Adhesion*, 2003, vol. 79, pp. 609-616.
Chen, X.; Wudl, F.; Mal, A.; Shen, H. Nutt, S.; "New Thermally Remendable Highly Cross-Linked Polymeric Materials" *Macromolecules*, 2003, vol. 36, pp. 1802-1807.
Chen, X.; Wudl, F.; Mal, A.; Shen, H. Nutt, S.; "A Thermally Re-mendable Cross-Linked Polymeric Material" *Science*, 2002, vol. 295, pp. 1698-1702.
McElhanon, J.; Russick, E.; Wheeler, D.;Loy, D.; Aubert, J.;"Removable Foams Based on an Epoxy Resin Incorporating Reversible Diels-Alder Adducts" *Journal of Applied Polymer Science*, 2002, vol. 85, pp. 1496-1502.
McElhanon, J.; Wheeler.; "Thermally Responsive Dendrons and Dendrimers Based on Reversible Furan-Maleimide Diels-Alder Adducts" *Organic Letters*, 2001, vol. 3(17), pp. 2681-2683.
Su, D.; Jeager, D.; "High regioselectivity in the Diels-Alder reaction of a surfactant dienophile resulting from a short tether between their functional groups and head groups," *Tetrahederon Letters*, 1999, vol. 40(45); pp. 7871-7874.
Masuyama, A.; Endo, C.; Takeda, S-Y.; Nojima; M; "Ozone-cleavable Gemini surfactants, a new candidate for an environmentally friendly surfactant" *Chemical Communications*, 1998, Issue 18, pp. 2023-2024.
Goussé, C.; Gandini, A.; Hodge P.; "Application of the Diels-Alder Reaction to Polymers Bearing Furan Moieties. 2. Diels-Alder and Retro-Diels-Alder Reactions Involving Furan Rings In Some Styrene Copolymers"; *Macromolecules*, 1998, vol. 31, pp. 314-321.
Park, J. O.; Jang, S. H.; "Synthesis and Characterization of Bismaleimides from Epoxy Resins" *Journal of Polymer Science: Part A: Polymer Chemistry*, 1992, vol. 30, pp. 723-729.
Hayashi, Y.; Shirai, F.; Shimizu, T.; Nagano, Y.; Teramura, K.; "Synthesis and Properties of 2-Alkoxy-N, N-Dimethylethylamine N-Oxides" *Journal of American Oil Chemists' Society*; 1985, vol. 62 (3), pp. 555-557.
Keana, J.; Guzikowski, A.; Morat, C.; Volwerk, J.; "Detergents Containing a 1,3-Diene Group in the Hydrophobic Segment. Facile Chemical Modification by a Diels-Alder Reaction Hydrophilic Dienophiles in Aqueous Solution," *The Journal of Organic Chemistry*, 1983, vol. 48(16), pp. 2661-2666.
Piancatelli, G.; Scettri, A.; D'Auria, M.; "Oxidative ring opening of furan derivatives to α,β-unsaturated γ-dicarbonyl compounds, useful intermediates for 3-oxocyclopentanes synthesis" *Tetrahederon*, 1980, vol. 36(5); pp. 661-663.
Khattab, SA; Khalifa, MA; Mahgoub, SA; "Diels-Alder Reactions with some N-Substituted Maleimides," *Journal fuer Praktische Chemie* (Liepzieg), 1977, vol. 319(3): pp. 432-438.

*Primary Examiner*—Rebecca Anderson
*Assistant Examiner*—Michael P. Barker
(74) *Attorney, Agent, or Firm*—Timothy P. Evans (57) ABSTRACT

The present invention describes surfactants of formula (I), $$R_N-N\underset{O}{\overset{O}{\diagup\!\!\!\diagdown}}\diagdown O-(R)_m \quad (I)$$

wherein R, $R_N$, and m are defined herein, processes for their preparation, and methods for their decomposition.

10 Claims, 4 Drawing Sheets

THERMALLY CLEAVABLE SURFACTANTS WITHOUT DEPROTONATION

CROSS REFERENCE TO RELATED APPLICATIONS

This application is a continuation-in-part of prior U.S. patent application Ser. No. 10/866,475 originally filed Jun. 10, 2004 now U.S. Pat. No. 7,022,861 entitled "THERMALLY CLEAVABLE SURFACTANTS", which is herein incorporated by reference in its entirety.

STATEMENT OF GOVERNMENT SUPPORT

The United States Government has a paid-up license in this invention and the right in limited circumstances to require the patent owner to license others on reasonable terms as provided for by the terms of contract No. DE-AC04-94AL85000 awarded by the U.S. Department of Energy to Sandia Corporation.

BACKGROUND OF THE INVENTION

1. Field of the Invention

The present invention relates to thermally labile surfactants prepared by Diels-Alder (hereinafter "DA") reactions. In particular, the invention relates to the sodium sulfonate thermally cleavable surfactant and processes for their preparation.

2. Description of the Related Art

Over the past decade, the development of cleavable surfactants has been a growing field in surfactant science. As the name implies, cleavable surfactants are molecules that undergo a chemical or physical change of the parent molecular structure resulting in a change and/or loss of surface-active behavior. Hence, the production of commercially available cleavable surfactants may find utility in industrial practices where foaming or persistent surface-active properties must be diminished after their initial use in "green" chemistry where degradability is of primary concern, and in biomedical drug delivery where surfactants could be removed through biological mechanisms.

To overcome these shortcomings, we describe here the synthesis and characterization of two new surfactant compositions which incorporate a thermally cleavable DA adduct as the chemical weak-link within the surfactant molecular structure. In particular, we have utilized the reversible DA reaction between functionalized furans and maleimides as the basis for thermally cleavable materials. We have previously reported the integration of furan-maleimide DA adducts into molecules to produce thermally responsive encapsulating polymers, foams, and adhesives as well as dendrons and dendrimers which reversibly self-assemble (see U.S. Pat. Ser. Nos. 6,271,335; 6,337,384; and 6,403,753; U.S. published application Ser. No. 20030116272; and Aubert, J. H., *Journal of Adhesion*, 2003, v. 79, pp. 609-616; McElhanon, J. R., et al., *Journal of Applied Polymer Science*, 2002, v. 85, p. 1496; and McElhanon, J. R., et al., *Organic Letters*, 2001, v. 3(17), p. 2681). Also, similar thermally reversible DA adducts have been reported incorporated into other responsive polymers (see Chen, X., et al., *Macromolecules*, 2003, v. 36, p1802-1807; and Chen, X., et al., *Science*, 2002, v. 295, p1698-1702).

We have previously reported on (McElhanon, J. R., et al., *Langmuir*, 2005, v. 21, pp. 3259-3266) the synthesis and characterization of surfactants that possess a furan-maleimide DA thermally activated weak-link. These surfactants possessed either carboxylate or phenolate polar head groups and a 12 carbon linear alkyl chain that served as the hydrophobic tail section. These surfactants all require deprotonation of the head group through addition of an excess of potassium hydroxide to achieve solubility in water. We present here the synthesis and characterization of two sulfonate-based sodium salt DA surfactants that require no deprotonation step or addition of hydroxide and are soluble in water and/ or polar organic solvents. The surfactants degrade into hydrophilic and hydrophobic fragments after exposure to elevated temperatures (>50° C.) and lose all surface-active behavior.

SUMMARY OF THE EMBODIMENTS

In a broad aspect, the invention describes compounds of formula (I), (I)

wherein $R_N$ is -L-G, wherein,

L is -aryl-, -heteroaryl-, -($C_8$-$C_{30}$)alkyl-, -($C_6$-$C_{20}$)haloalkyl-, -($C_3$-$C_{10}$)cycloalkyl-, or -heterocyclyl-; and G is —$S(O)_2OM$, wherein M is H, Li, Na, K, Rb, or Cs;

R is -$L_1$-R', wherein, $L_1$ is a bond, -($C_1$-$C_4$)alkyl-O—, -aryl-, or -($C_3$-$C_{10}$) cycloalkyl-; and R' is -($C_8$-$C_{30}$)alkyl, -($C_6$-$C_{20}$)haloalkyl, or -(($C_1$-$C_4$) alkyl- O)$_j$-R", wherein j is an integer from 2 to 100; and R" is —H or methyl; and m is an integer from 1 to 4.

The invention further describes a process for the preparation of compounds of formula (I).

In a further aspect, the invention describes a method for the decomposition of surfactants according to formula (I), comprising heating the surfactant above about 55° C. in an optional polar organic solvent.

DETAILED DESCRIPTION OF THE INVENTION

In another aspect, the invention describes the compound according to formula (I), wherein:
$R_N$ is -L-G, wherein
  L is -aryl-, -($C_8$-$C_{30}$)alkyl-, or -($C_6$-$C_{20}$)haloalkyl-; and
  G is —S(O)$_2$OM,
    wherein M is H, Li, Na, K, Rb, or Cs; and
R and m are as defined in formula (I).

In another aspect, the invention describes the compound according to formula (I), wherein:
R is -$L_1$-R', wherein,
  $L_1$ is a bond or -($C_1$-$C_4$)alkyl-O—; and R' is -($C_8$-$C_{30}$)alkyl or -($C_6$-$C_{20}$)haloalkyl; and
$R_N$ and m are as defined in formula (I).

In a preferred aspect, the invention describes the compound of formula (II), (II)

wherein G, R, and m are as defined in formula (I).

In another aspect, the invention describes the compound of formula (II), wherein
  m is 1 or 2; and
  G and R are as defined in formula (I).

In a more preferred aspect, the invention describes the compound according to of formula (III), (III)

wherein G and R are as defined in formula (I).

In another aspect, the present invention describes the compound of formula (III), wherein:
R is -$L_1$-R', wherein,
  $L_1$ is a bond; and
  R' is -($C_8$-$C_{30}$)alkyl or -($C_6$-$C_{20}$)haloalkyl; and
G is as defined in formula (I).

In another aspect, the present invention describes the compound of formula (III), wherein:
R is -$L_1$-R', wherein,
  $L_1$ is a bond; and
  R' is -($C_8$-$C_{30}$)alkyl; and
G is as defined in formula (I).

In another aspect, the present invention describes a process to prepare a compound of formula (I), comprising the steps of:

(i) contacting a furanyl compound of formula (IV), (IV)

wherein:
R is -$L_1$-R', wherein,
  $L_1$ is a bond, -($C_1$-$C_4$)alkyl-O-, -aryl-, or -($C_3$-$C_{10}$)cycloalkyl-; and
  R' is -($C_8$-$C_{30}$)alkyl, -($C_6$-$C_{20}$)haloalkyl, or -(($C_1$-$C_4$)alkyl- O)$_j$-R", wherein:
    j is an integer from 2 to 100; and R" is —H or methyl; and
  m is an integer from 1 to 4;

with a maleimide compound of formula (V), (V)

wherein
$R_N$ is -L-G, wherein:
  L is -aryl-, -heteroaryl-, -($C_8$-$C_{30}$)alkyl-, -($C_6$-$C_{20}$)haloalkyl-, -($C_3$-$C_{10}$)cycloalkyl-, or -heterocyclyl-; and
  G is —S(O)$_2$OM,
    wherein M is H, Li, Na, K, Rb, or Cs;

in an optional polar organic solvent; and
  (ii) heating the composition to a temperature of about 25° C. to about 55° C.

In another aspect, the invention describes the process to prepare a compound of formula (I), comprising the steps of
  (i) contacting a furanyl compound of formula (IV), wherein:
    $R_N$ is -L-G, wherein
      L is -aryl-, -($C_8$-$C_{30}$)alkyl-, or -($C_6$-$C_{20}$)haloalkyl-; and
      G is —S(O)$_2$OM,
        wherein M is H, Li, Na, K, Rb, or Cs;

with a maleimide compound of formula (V), in an optional polar organic solvent; and
  (ii) heating the composition to a temperature of about 25° C. to about 55° C.

In another aspect, the invention describes the process to prepare a compound of formula (I), comprising the steps of:
  (i) contacting a furanyl compound of formula (IV), with a maleimide compound of formula (V), wherein
    R is -$L_1$-R', wherein,
      $L_1$ is a bond or -($C_1$-$C_4$)alkyl-O—; and
      R' is -($C_8$-$C_{30}$)alkyl or -($C_6$-$C_{20}$)haloalkyl;
    in an optional polar organic solvent; and
  (ii) heating the composition to a temperature of about 25° C. to about 55° C.

In another aspect, the invention describes the process to prepare a compound of formula (I), comprising the steps of
  (i) contacting a furanyl compound of formula (IV), with a maleimide compound of formula (VI),

(VI)

wherein G is —S(O)$_2$OM,
wherein M is H, Li, Na, K, Rb, or Cs; in an optional polar organic solvent; and
(ii) heating the composition to a temperature of about 25° C. to about 55° C.

In a preferred aspect, the invention describes the process to prepare a compound of formula (I), comprising the steps of
(i) contacting a furanyl compound of formula (IV), with a maleimide compound which is N-(4-sodium sulfophenyl) maleimide, in an optional polar organic solvent; and
(ii) heating the composition to a temperature of about 25° C. to about 55° C.

In another aspect, the invention describes the process to prepare a compound of formula (I), comprising the steps of
(i) contacting a furanyl compound of formula (IV), wherein m is 1 or 2; with a maleimide compound of formula (V), in an optional polar organic solvent; and
(ii) heating the composition to a temperature of about 25° C. to about 55° C.

In another aspect, the invention describes the process to prepare a compound of formula (I), comprising the steps of
(i) contacting a furanyl compound of formula (VII), (VII)

with the maleimide compound as defined in formula (V), in an optional polar organic solvent; and
(ii) heating the composition to a temperature of about 25° C. to about 55° C.

In another aspect, the invention describes the process to prepare a compound of formula (I), comprising the steps of
(i) contacting a furanyl compound of formula (VII), wherein:
R is -L$_1$-R', wherein,
L$_1$ is a bond or -(C$_1$-C$_4$)alkyl-O—; and
R' is -(C$_8$-C$_{30}$) alkyl or -(C$_6$-C$_{20}$) haloalkyl;
with the maleimide as defined in formula (V), in an optional polar organic solvent; and
(ii) heating the composition to a temperature of about 25° C. to about 55° C.

In a preferred aspect, the invention describes the process to prepare a compound of formula (I), comprising the steps of
(i) contacting a furanyl compound which is 2-docecylfuran or 2-octadecyfuran, with the maleimide compound as defined in formula (V), in an optional polar organic solvent; and
(ii) heating the composition to a temperature of about 25° C. to about 55° C.

In a more preferred aspect, the invention describes the process to prepare a compound of formula (I), comprising the steps of
(i) contacting a furanyl compound which is 2-docecylfuran or 2-octadecyfuran, with the maleimide compound which is N-(4-sodium sulfophenyl) maleimide, in an optional polar organic solvent; and
(ii) heating the composition to a temperature of about 25° C. to about 55° C.

In a preferred aspect, the present invention describes the process to prepare a compound of formula (I), comprising the steps of
(i) contacting a furanyl compound of formula (IV) with a maleimide compound of formula (V), in an optional polar organic solvent which is N,N-dimethylformamide, and
(ii) heating the composition to a temperature of about 25° C. to about 55° C.

In another aspect, the present invention describes the process to prepare a compound of formula (I), comprising the steps of
(i) contacting a furanyl compound of formula (IV) with a maleimide compound of formula (V), in an optional polar organic solvent which is water, methanol, ethanol, i-propanol, t-butanol, glyme, diglyme, tetrahydrofuran, acetonitrile, dimethylsulfoxide, N,N-dimethylfuran, N,N-dimethylacetamide, N-methylpyrridinone, or mixtures thereof, and (ii) heating the composition to a temperature of about 25° C. to about 55° C.

In another aspect, the present invention describes the process to prepare a compound of formula (I), comprising the steps of
(i) contacting a furanyl compound of formula (IV) with a maleimide compound of formula (V), in an optional polar organic solvent, and
(ii) heating the composition to a temperature of about 30° C. to about 55° C.

In another aspect, the present invention describes the process to prepare a compound of formula (I), comprising the steps of
(i) contacting a furanyl compound of formula (IV) with a maleimide compound of formula (V), in an optional polar organic solvent, and
(ii) heating the composition to a temperature of about 40° C. to about 55° C.

In another aspect, the present invention describes the process to prepare a compound of formula (I), comprising the steps of
(i) contacting a furanyl compound of formula (IV) with a maleimide compound of formula (V), in an optional polar organic solvent, and
(ii) heating the composition to a temperature of about 45° C. to about 55° C.

In a preferred aspect, the present invention describes the process to prepare a compound of formula (I), comprising the steps of
(i) contacting a furanyl compound of formula (IV) with a maleimide compound of formula (V), in an optional polar organic solvent, and
(ii) heating the composition to a temperature of about 50° C. to about 55° C.

The present invention also describes a method for decomposing surfactants according to claim 1, comprising heating the surfactant to from about 55° C. to about 120° C. in an optional polar organic solvent.

The present invention also describes a method for decomposing surfactants according to claim 1, comprising heating the surfactant to from about 75° C. to about 120° C. in an optional polar organic solvent.

The present invention also describes a method for decomposing surfactants according to claim 1, comprising heating the surfactant to from about 85° C. to about 120° C. in an optional polar organic solvent.

The present invention also describes a method for decomposing surfactants according to claim 1, comprising heating the surfactant to from about 95° C. to about 120° C. in an optional polar organic solvent.

Preparations

Figure 1:
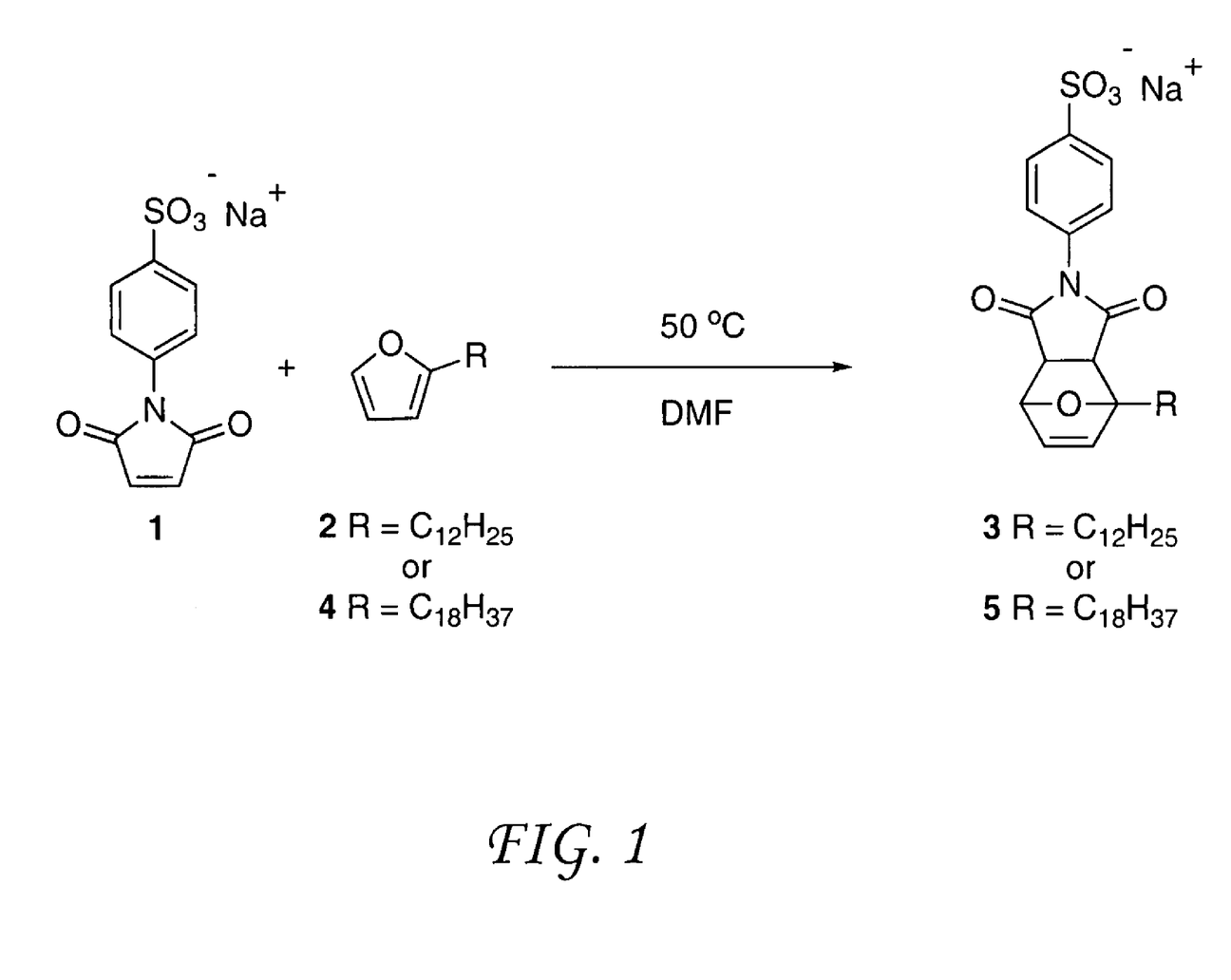
FIG. 1 illustrates the general scheme for synthesis of sulfonate DA surfactants 3 and 5.

The surfactants of the present embodiment comprise simple ringed adduct species constructed by the well-known DA reaction between appropriately functionalized furans and maleimides as the basis for these embodiments (FIG. 1). As mentioned, the process of adduct formation typically occurs at moderate temperatures (i.e., about 50° C.), whereas dissociation occurs at temperatures above about 55° C. Surfactant molecules that contain the furan-maleimide DA adducts are, therefore, attractive candidates as surface active materials for processes that require surfactant "deactivation" or removal using a non-invasive thermal trigger.

The examples of the present invention should not be construed as limiting the scope of the invention to any particular functional substituent. Surfactants contemplated as falling within the scope and meaning of the present invention, therefore, may use any of the head and tail groups known to the surfactant science arts that can be incorporated into the precursor molecules forming the basis for the DA cycloaddition reaction. In particular, tail groups comprising long alkyl chains, with or without branching, having the general formula $C_nH_{2n}$ where n varies from 6 to about 24 and preferably from 6 to about 18, are considered as within the scope of the present disclosure as are any of the headgroups comprising a sodium sulfonate group.

An alkylfuran is used as the diene molecule and a maleimide incorporating a sodium sulfophenyl group as the dienophile molecule to produce the desired DA adduct molecules of the present invention. In this way the alkylfuran carries with it the non-polar (hydrophobic) "tail" group for the nascent surfactant molecule while the maleimide carries the to polar (hydrophilic) "head" group of the surfactant molecule as these two molecules are combined by the DA process. The alkylfuran is prepared as generally described by Piancatelli, et al., (*Tetrahedron*, 1980, v. 36(5), pp. 661-663, herein incorporated by reference) by a reaction between furan and an alkyl bromide molecule in a solution of n-butyl lithium and THF. The functional maleimide is prepared as described by Park, et al., (*Journal of Polymer Science Part A: Polymer Chemistry*, 1992, v. 30(5), pp. 723-729, herein incorporated by reference) by a condensation reaction to provide the sodium sulfophenyl maleimide.

Definitions

The term "alkyl" as used herein, means a hydrocarbon chain of 1 to 30 carbons, wherein the chain is linear or branched at any point therein. Examples of alkyl groups include, but are not limited to, methyl, propyl, i-propyl, t-butyl, 2-ethylhexyl, n-decyl, n-eicosyl, and the like.

The term "aryl" as used herein, means a cyclic aromatic hydrocarbon containing 5 to 14 carbons, wherein the group may be monocyclic or fused bicyclic or tricyclic groups. Examples of aryl groups include, but are not limited to, phenyl, naphthyl, anthracenyl, and the like.

The term "polar organic solvent" as used herein, means a solvent with a dielectric constant greater than 6. Examples of polar organic solvents include, but are not limited to, water, dimethylsulfoxide, methylene chloride, tetrahydrofuran, methanol, and the like.

The term "cycloalkyl" as used herein, means a saturated cyclic hydrocarbon containing 3 to 10 carbons, wherein the rings may be monocyclic, fused or bridged bicyclic, and fused or bridge tricyclic. Examples of cycloalkyl groups include, but are not limited to, cyclopropyl, cyclohexyl, bicyclo[2.2.2]octyl, adamantyl, decalinyl, and the like.

The term "heterocyclyl" as used herein, means a saturated cyclic group containing at least one heteroatom, such as N, O, S, or P, and containing 3 to 10 total atoms in the ring system. The ring system may be monocyclic, fused or bridged bicyclic, or fused or bridged tricyclic. Examples of heterocyclyl groups include, but are not limited to tetrahydrofuranyl, pyrrilodinyl, piperidinyl, piperazinyl, aziridinyl, oxiranyl, morpholinyl, thiomorpholinyl, and the like.

The term "heteroaryl" as used herein, means an aromatic cyclic group containing at least one heteroatom, such as N, O, S, or P, and containing 5 to 14 total atoms in the ring system. The ring system may be monocyclic, fused bicyclic, or fused tricyclic. Examples of heteroaryl groups include, but are not limited to, pyridyl, pyrrolyl, thienyl, furanyl, quinolinyl, indolyl, isoindolyl, isoquinolinyl, and the like.

The term "haloalkyl" as used herein, means an alkyl group, as defined herein, substituted with one or more halogen groups, as defined herein. Examples of haloalkyl groups include, but are not limited to trifluoromethyl, nonafluorobutyl, 2,2,2-trifluoroethyl, 1,1- bis(trifluoromethyl)-2,2,2-trifluoroethyl-, 2-chloroethyl, 2,2,2-trichloroethyl, dibromomethyl, 3-bromopropyl, iodomethyl, and the like.

The term "halogen" as used herein means fluoro, chloro, bromo, or iodo.

EXAMPLES

Example 1 exo-4-Dodecyl-7-oxabicyclo[2.2.1]hept-5-ene-2,3-dicarboxy-N- (4-sodium sulfophenyl)imide (Compound 3)

To a solution of N-(4-sodium sulfophenyl)maleimide 1 (6.12 g, 22.2 mM) in DMF (40 mL) was added 2-dodecylfuran 2 (26.3 g, 0.11 M). The reaction was allowed to stir at 50° C. until $^1$H NMR showed consumption of maleimide starting material 1. The reaction was then concentrated to dryness and the residue washed with petroleum ether until excess 2- dodecylfuran 2 was removed to yield surfactant molecule 3 (10.7 g, 94%) as a tan solid. Surfactant 3 was isolated as a mixture of 96:4 exo/endo isomers.

NMR spectra were measured at 500 MHz $^1$H and at 125 MHz $^{13}$C, in DMSO-$d_6$. Spectral results are as follows:

$^1$H NMR (500 MHz, DMSO-$d_6$) exo δ 7.69 (d, J=8.5 Hz, 2H), 7.15 (d, J=8.5 Hz, 2H), 6.57 (dd, J=5.0, 2.0 Hz, 1H), 6.51, (d, J=5.5 Hz, 1H), 5.28 (dd, J=5.0, 1.5 Hz, 1H), 3.17 (d, J=6.5 Hz, 1H), 2.94 (d, J=6.5 Hz, 1H), 2.04-1.98 (m, 1H), 1.84-1.78 (m, 1H), 1.57-1.53 (m, 1H), 1.45-1.39 (m, 1H), 1.32-1.13 (m, 18H), 0.84 (t, J=7.0 Hz, 3H).

$^{13}$C NMR (125 MHz, DMSO-$d_6$) exo δ 175.54, 174.10, 148.13, 138.79, 137.00, 132.04, 126.16, 126.15, 91.44, 80.22, 50.47, 49.06 31.27, 29.43, 29.03, 29.00, 28.98, 28.94, 28.92, 28.68, 24.73, 22.07, 13.93.

Example 2 exo-4-Octadecyl-7-oxabicyclo[2.2.1]hept-5-ene-2,3-dicarboxy-N-(4-sodium sulfophenyl)imide (Compound 5)

To a solution of N-(4-sodium sulfophenyl)maleimide 1 (2.02 g, 7.34 mM) in DMF (20 mL) was added 2-octyldecylfuran 4 (11.7 g, 37.9 mM). The reaction was allowed to stir at 50° C. until $^1$H NMR showed consumption of maleimide starting material 1. The reaction was then concentrated to dryness and the residue washed with petroleum ether until excess 2-octyldecylfuran 4 was removed to yield surfactant molecule 5 (4.21 g, 96%) as a brown solid.

NMR spectra were measured at 500 MHz $^1$H and at 125 MHz $^{13}$C, in DMSO-$d_6$. Spectral results are as follows:

$^1$H NMR (500 MHz, DMSO-$d_6$) exo δ 7.68 (d, J=8.5 Hz, 2H), 7.15 (d, J=8.5 Hz, 2H), 6.58 (dd, J=5.0, 1.5 Hz, 1H), 6.51, (d, J=6.0 Hz, 1H), 5.13 (dd, J=5.0, 1.5 Hz, 1H), 3.17 (d, J=6.5 Hz, 1H), 2.94 (d, J=6.5 Hz, 1H), 2.04-1.98 (m, 1H), 1.84-1.78 (m, 1H), 1.56-1.14 (m, 30H), 0.84 (t, J=6.5 Hz, 3H).

$^{13}$C NMR (125 MHz, DMSO-$d_6$) exo δ 175.52, 174.07, 148.30, 138.78, 136.99, 131.94, 126.12, 126.04, 91.42, 80.19, 50.45, 49.05 31.25, 29.42, 28.99, 28.98, 28.96, 28.92, 28.66, 24.73, 22.06, 13.92.

Example 3

Characterization of Aqueous Surfactant Solutions

The surfactants were characterized in terms of their critical micelle concentration (hereinafter "cmc"). This was achieved through dynamic surface tension measurements and dye solubilization.

Example 3a

Determination of Critical Micelle Concentration by Dynamic Surface Tension

The dynamic surface tension measurements were conducted using a SENSADYNE® QC3000 dynamic surface tensiometer (available from the SENSADYNE® Instruments Division of the Chem-Dyne Research Corporation, Mesa, Ariz.) that utilizes the maximum bubble pressure method. The fundamental operating principles and theoretical considerations of this method are explained in detail elsewhere, and a brief summary only is given here. Two glass probes with different orifice diameters (0.5 and 4.0 mm) were submerged in an aqueous surfactant solution and nitrogen was bubbled through the samples. Dry nitrogen was used as the bubble source gas and was delivered to the instrument at 50 psi. The instrument was operated at a bubble frequency of 0.5 Hz to approximate equilibrium surface tension values for each sample. The differential pressure signal generated by bubble formation is related to the interfacial surface tension of the liquid and gas. Surface tension calibration was carried out by measuring the surface tension of deionized water and ethanol and comparing to known literature values. Solution temperature was monitored with a calibrated thermistor (± 0.1° C.) attached to the orifice probes. Instrumental calibration was conducted for every change in experimental conditions and after prolonged periods of instrumental quiescence. All experiments were conducted at 25.0±0.2° C. unless otherwise noted. Time averaging of the data produced values that differed by less than 0.2 mN/m from the mean.

Example 3b

Determination of Critical Micelle Concentration by Dye Solubility

To determine the enhanced solubility of a water-insoluble dye (Orange OT) in the presence of the oily cores of micelles that exist above the critical micelle concentration, an excess amount (0.02 g per 10 mL of aqueous sample) of the dye was added to a series of aqueous surfactant solutions and ultrasonically agitated using a SONICATOR® for 30 minutes in a water bath operated under ambient conditions. The solutions were then removed from the SONICATOR® and allowed to settle under ambient conditions for 2 hours. The solutions were filtered using 0.2 µm polyvinylidene fluoride (PVDF) syringe filters (obtained from Whatman Inc., Florham Park, N.J.) into 3.5 mL 1 cm path length quartz cuvettes (available from Starna Cells, Inc., Atascadero, Calif.). The amount of dye solubilized in each sample was measured by monitoring the absorbance wavelength of each with a Shimadzu 2401-PC UV-Vis Dual Beam Spectrophotometer (obtained from Shimadzu Scientific Instruments (SSI), Pleasanton, Calif.) operating at ambient conditions with surfactant solutions without dyes serving as the sample background.

Example 4

Results of CMC Determinations

Figure 2:
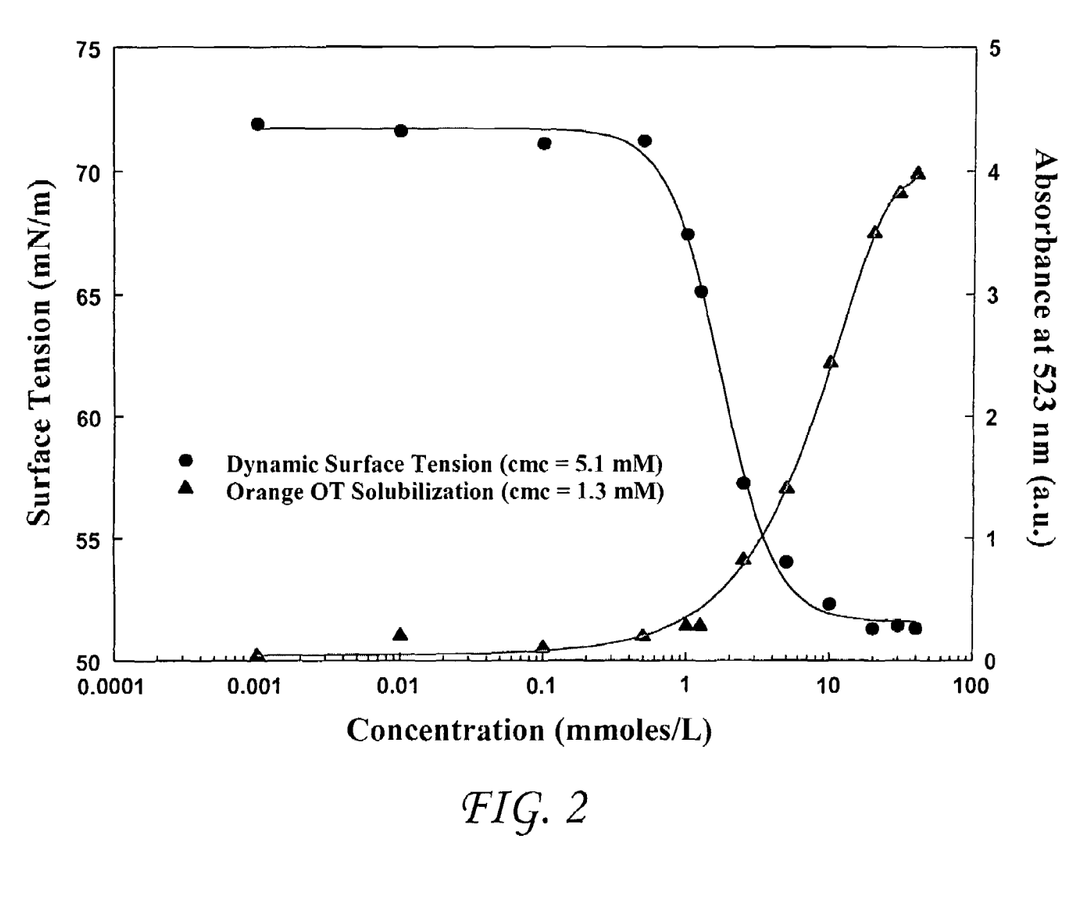
FIG. 2 graphically illustrates the critical micelle concentration (cmc) determination of the furan-maleimide dodecyl sulfonate sodium salt surfactant 3.

The results obtained from surface tension measurements as a function of concentration for surfactant 3 are presented in FIG. 2. The data follows the classic surface-active profile plot, with two distinct inflection points followed by plateau regions. The first inflection point, occurring at very low concentrations, indicates the initial surfactant adsorption at the gas-liquid interface that lowers the effective surface tension of the liquid. The relationship between concentration and surface tension is relatively monotonic at concentrations greater than this lower inflection point. The second inflection point, which occurs near 5 mM, is the result of the formation of a fully saturated gas-liquid interface by the surfactant, and it is at this point that micelles begin to form. The surface tension values above this concentration are observed to remain relatively constant.

The results from determination of cmc for surfactant 3 using dye solubility are also presented in FIG. 2. It can be seen that at low concentrations (<1 mM), very little dye is present in the aqueous samples, which is in agreement with the published solubility data for the dye. Once the concentration is increased above 1 mM, however, there is a marked increase in the observed dye absorbance at 523 nm (the anticipated peak absorbance wavelength). This indicates that more of the oil-soluble dye is present in solution. The increase in the apparent solubility of the dye is explained by the presence of micelles that possess "oily" cores that are favorable to the dye. As the concentration is increased, the amount of dye is also observed to increase in a monotonic fashion. This is due to an increase in the number of micelles present in solution as the concentration is increased beyond the cmc.

The cmc of the dodecyl sulfonate sodium salt surfactant is therefore determined to be 1.3 mM through dye solubilization and 5.1 mM by dynamic surface tension measurements. This apparent discrepancy is explained by the fact that one (dye solubilization) is a static probe of the micellar environment, whereas the other (dynamic surface tension) is a dynamic probe of the gas-liquid interface. The dynamic probe will always produce higher apparent values of the cmc as it is creating a new gas-liquid interface and thus decreases the amount of bulk surfactant in solution over time.

Example 5

Demonstration of retro-DA degradation via Surface tension

Figure 3:
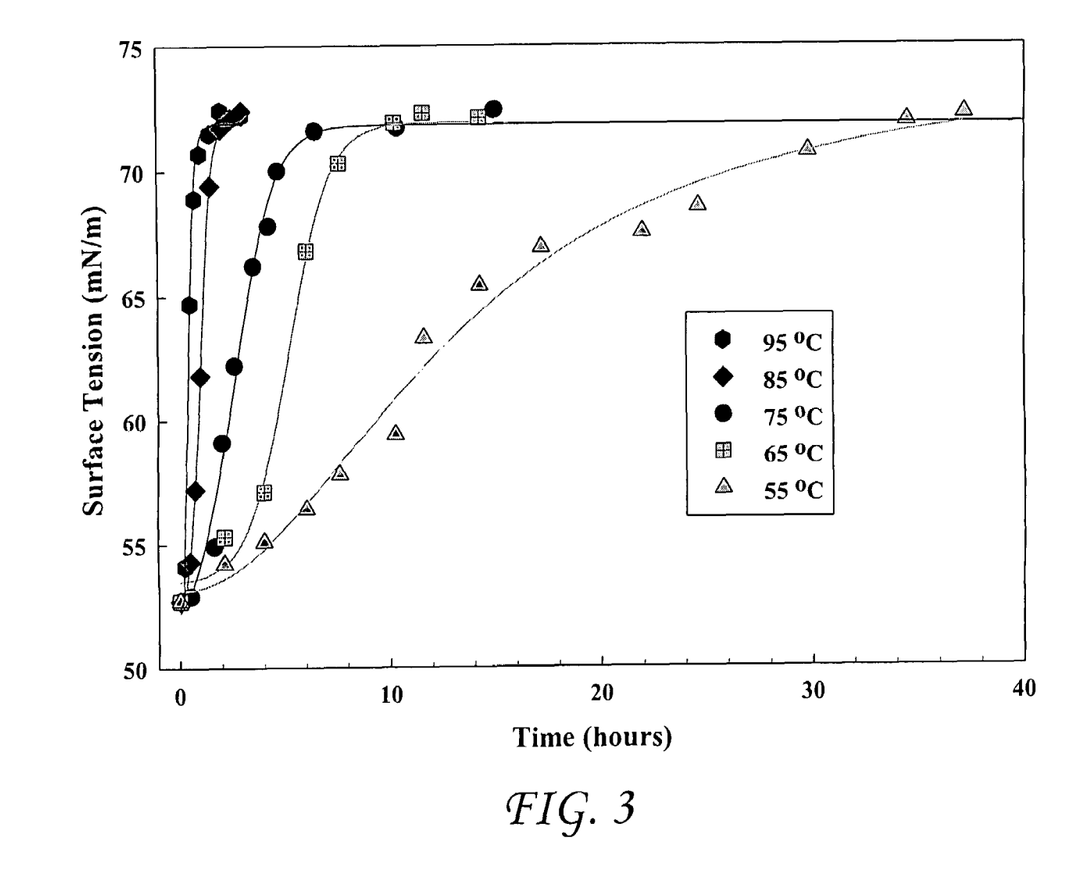
FIG. 3 graphically illustrates the rate of dissociation dependence on temperature for sulfonate DA surfactant 3.

The surfactants of the invention undergo the retro-DA reaction after exposure to elevated temperatures. To determine the effect of temperature on surface tension as a measurement of surfactant degradation, 10 mM (2× cmc as determined by surface tensiometry) solutions of the surfactants in water were prepared. Data were recorded for all experiments via a computer interface using the SENSADYNE® QC3000 version 5.3 software. The data obtained from these experiments is presented in FIG. 3 and indicates that the surfactants possess different rates of degradation based on the temperatures to which they are exposed.

Additional measurements to determine the effect of temperature on the rates of surfactant dissociation and loss of surface active properties were conducted on 10 mM solutions of surfactant 3. The data shown in FIG. 3 clearly indicate that the temperature at which the samples are elevated to has a dramatic impact on the rate at which the surface active properties are lost in these solutions. At the highest temperature, 95° C., there is a loss of all surface activity and the surface tension is that of water within 1 hour of exposure. At the lowest temperature monitored, 55° C., it takes over 30 hours of exposure to eliminate surface activity. The data has been fit with a logistic 4-parameter algorithm using SIGMAPLOT® (available from Systat Software, Inc., Richmond, Calif.). The resultant fits to the data are reasonable and are within 5% error and achieved $R^2$ values greater than 99.0%. This data provides the baseline for "tailoring" the surface activity of a system based on at least three parameters: (a) initial surfactant concentration utilized, (b) temperature, and (c) time at temperature. The effective control of the surface active properties of the system is envisioned to be accomplished by manipulating one or any combination of these parameters. It should also be noted that all of the surface tension measurements of the cleaved samples were taken after the samples had cooled to ambient conditions, and are convincing evidence that the dissociation accompanying the retro DA is irreversible in micelles.

Example 6

Demonstration of retro-DA degradation via NMR

Figure 4A:
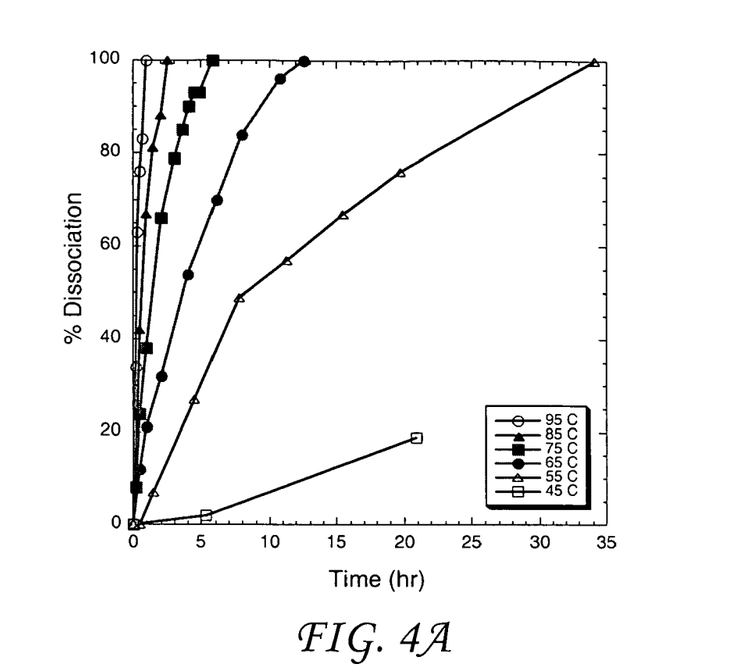
FIG. 4A graphically illustrates the rate of dissociation for 10 mM aqueous solutions of sulfonate DA surfactants 3.
Figure 4B:
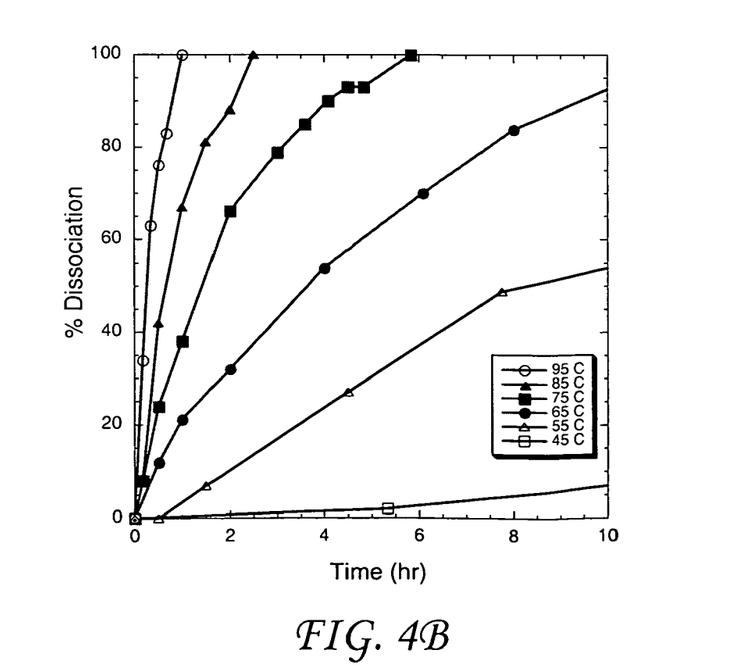
FIG. 4B illustrates an expanded view of FIG. 4A up to 10 hours.

Detailed solution-based thermal degradation experiments on surfactant 3 were also monitored by $^1$H NMR to elucidate degradation rates at a variety of temperatures. The data for 10 mM aqueous samples of surfactant 3 heated isothermally over time are shown in FIGS. 4A and 4B. Percent degradation was tracked by recording the decrease in the integral value for the bridge head proton of the DA adduct located at 5.02 ppm. At the highest temperature tested, 95° C., surfactant 5 was completely degraded after about 1 hour of heating. At 65° C., surfactant 3 completely degraded after about 10 hours of heating. It is important to note that the percent degradation of surfactant 5 over various temperatures is not necessarily linear. This is a result of the $K_{eq}$ for the reversible DA reaction with DA adduct formation/stability dominating at lower temperatures.

Finally, to the extent necessary to understand or complete the disclosure of the present invention, all 20 publications, patents, and patent applications mentioned herein are expressly incorporated by reference therein to the same extent as though each were individually so incorporated.

Having thus described exemplary embodiments of the present invention, it should be noted by those skilled in the art that the disclosures herein are exemplary only and that various other alternatives, adaptations, and modifications may be made within the scope of the present invention. Accordingly, the present invention is not limited to the specific embodiments as illustrated herein, but is only limited by the following claims.

We claim:

1. A compound of formula (I), wherein $R_N$ is -L-G, wherein
  L is -aryl-, -heteroaryl-, -($C_8$-$C_{30}$)alkyl-, -($C_6$-$C_{20}$)haloalkyl-, -($C_3$-$C_{10}$) cycloalkyl-, or -heterocyclyl-; and
  G is —S(O)$_2$OM,
    wherein M is H, Li, Na, K, Rb, or Cs;
R is -$L_1$-R', wherein,
  $L_1$ is a bond, -($C_1$-$C_4$)alkyl-O-, -aryl-, or -($C_3$-$C_{10}$)cycloalkyl-; and
  R' is -($C_8$-$C_{30}$) alkyl, -($C_6$-$C_{20}$)haloalkyl, or -(($C_1$-$C_4$) alkyl-O)$_j$-R", wherein
    j is an integer from 2 to 100; and
    R" is —H or methyl; and
m is an integer from 1 to 4.

2. The compound according to claim 1, wherein
$R_N$ is -L-G, wherein
  L is -aryl-, -($C_8$-$C_{30}$)alkyl-, or -($C_6$-$C_{20}$)haloalkyl-; and
  G is —S(O)$_2$OM,
    wherein M is H, Li, Na, K, Rb, or Cs.

3. The compound according to claim 1, wherein
R is -$L_1$-R', wherein,
  $L_1$ is a bond or -($C_1$-$C_4$)alkyl-O-; and
  R' is -($C_8$-$C_{30}$)alkyl or -($C_6$-$C_{20}$)haloalkyl.

4. The compound according to claim 1, of formula (II),

5. The compound according to claim 4, wherein m is 1 or 2.

6. The compound according to claim 4, of formula (III),

7. The compound according to claim 6, wherein
R is -$L_1$-R', wherein,
  $L_1$ is a bond; and
  R' is -($C_8$-$C_{30}$)alkyl or -($C_6$-$C_{20}$)haloalkyl.

8. The compound according to claim 7, wherein R' is -($C_8$-$C_{30}$) alkyl.

9. The compound according to claim 1 which is exo-4-octadecyl-7-oxabicyclo[2.2.1]hept-5-ene-2,3-dicarboxy-N-(4-sodium sulfophenyl)imide.

10. The compound according to claim 1 which is exo-4-dodecyl-7-oxabicyclo[2.2.1]hept-5-ene-2,3-dicarboxy-N-(4-sodium sulfophenyl)imide.

* * * * *